(12) United States Patent
van Doormalen (10) Patent No.: US 9,179,637 B2
(45) Date of Patent: Nov. 10, 2015

(54) LEEK VARIETY NUN 08412

(75) Inventor: Toon van Doormalen, Meijel (NL)

(73) Assignee: Nunhems B.V., AC Nunhem (NL)

( * ) Notice: Subject to any disclaimer, the term of this patent is extended or adjusted under 35 U.S.C. 154(b) by 571 days.

(21) Appl. No.: 13/559,774

(22) Filed: Jul. 27, 2012

(65) Prior Publication Data

US 2013/0202775 A1 Aug. 8, 2013

(51) Int. Cl.
*A61H 5/00* (2006.01)
*A01H 5/12* (2006.01)

(52) U.S. Cl.
CPC ........................................ *A01H 5/12* (2013.01)

(58) Field of Classification Search
None
See application file for complete search history.

(56) References Cited

U.S. PATENT DOCUMENTS

| | | | |
|---|---|---|---|
| 2011/0167509 A1* | 7/2011 | Van Cappellen et al. | 800/260 |
| 2013/0291219 A1* | 10/2013 | Larkins et al. | 800/275 |
| 2014/0072693 A1* | 3/2014 | Waycott | 426/615 |
| 2014/0223669 A1* | 8/2014 | Corona et al. | 8/137 |
| 2014/0224707 A1* | 8/2014 | Haroun et al. | 208/108 |
| 2014/0228479 A1* | 8/2014 | Darnaud et al. | 523/156 |

OTHER PUBLICATIONS

Fehr "Backcross Method" (1987) Iowa State University, "Principles of Cultivar Development," vol. 1 Theory and Technique and vol. 2 Crop Species, Soybean, Macmillian Publishing Company, New York; pp. 360-376.*
British Dictionary (via Websters.com) definition of essentially.*
UPOV descriptors are the plant variety descriptors described for leek in the Guidelines for the Conduct of Tests for Distinctness, Uniformity and Stability, TG/85/7 (Geneva 2008), as published by UPOV (International Union for the Protection of New Varieties and Plants, http://www.upov.int/edocs/tgdocs/en/tg085.pdf.
Eugenia Martin, et al., Identification of markers linked to agronomic traits in globe artichoke, Australian Journal of Crop Science (2008) vol. 1(2), pp. 43-46.
Jack E. Staub, et al., Comparative analysis of cultivated melon groups (*Cucumis melo* L.) using random amplified polymorphic DNA and simple sequence repeat markers, Euphytica (2000) vol. 115, pp. 225-241.
Peter Vos, et al., AFLP: a new technique for DNA fingerprinting 1995, Nucleic Acids Research (1995) vol. 23, No. 21, pp. 4407-4414.
Variety Tracer method of the Nak Tuinbouw (http://www.naktuinbouw.nl/en/topic/identification-using-dna), downloaded on Jul. 27, 2012.

* cited by examiner

*Primary Examiner* — Cathy Kingdon Worley (57) ABSTRACT

The invention relates to the field of *Allium ampeloprasum* var. *porrum* (L.), in particular to a new variety of *Allium porrum* designated NUN 08412, a sample of seed of said variety having been deposited under Accession Number NCIMB 42445, plants and leek leaves thereof.

19 Claims, 1 Drawing Sheet

LEEK VARIETY NUN 08412

FIELD OF THE INVENTION

The present invention relates to the field of plant breeding. In particular, a new and distinct hybrid variety of leek is provided, designated NUN 08412.

Provided are seeds of NUN 08412; plants and plant parts produced from these seeds such as (harvested) leaves or parts thereof, pollen, cells, petioles, shoots or parts thereof, stems or parts thereof, roots or parts thereof, cuttings or parts thereof, flowers; vegetative reproductions of the variety NUN 08412; and progeny of the variety.

Leek (*Allium ampeloprasum* var. *porrum* (L.) or *Allium porrum*) belongs to the Alliceae family and is used as a crop in diverse countries. Most of the commercially available leek varieties are leek hybrid plants. These leek hybrid plants are plants produced by crossing a selected leek population with another selected leek population. The leek hybrid plants provide advantages over open pollinated crossbreds, such as uniformity, vitality and disease tolerance, resulting in an increased use of leek hybrids in commercial leek productions. Leek hybrid plants are generally produced by a technique designated in the art as "nuclear male sterility". Nuclear male sterility is a form of male sterility wherein the genetic factor responsible for the observed sterility is encoded by the nuclear genome. The term "Male sterility" indicates that a plant has no fertile pollen and, because of this, the male sterile plant is incapable of self-pollination.

Rather than forming a tight bulb like the onion, the leek produces a long cylinder of bundled leaf sheaths which are generally blanched by pushing soil around them (trenching). They are often sold as small seedlings in flats which are started off early in greenhouses, to be planted out as weather permits. Once established in the garden, leeks are hardy; many varieties can be left in the ground during the winter to be harvested as needed.

Leek cultivars can mainly be divided in three types: Summer leek, Autumn leek and Winter leek.

Summer leek is fast growing leek, leaf color is green. Harvest period is early summer to late summer/beginning of autumn.

Autumn leek is medium fast to medium slow growing leek. Leaf color is dark green to blue-green. Varieties are more tolerant to low temperatures. Most genotypes in this type have a shorter shaft compared to the summer leek. Harvest period is early autumn, autumn, beginning of winter.

Winter leek is slow growing leek. Foliage color is dark green mostly blue-green; varieties are tolerant to cold and to frost to some extent. Winter hardiness is good. Shafts are rather short. Harvest period is end of autumn, winter until early spring (just before bolting starts).

The edible portions of the leek are the white base of the leaves (above the roots and stem base), the light green parts, and to a lesser extent the dark green parts of the leaves. One of the most popular uses is for adding flavor to stock.

The use of a type of leek depends on the growth habit of said leek and a customer's preference for shape of leaves/the plant, and color. There is thus a need for new leek with unique shape and color properties.

SUMMARY OF THE INVENTION

In one aspect of the invention, a seed of leek variety NUN 08412 is provided, wherein a representative sample of said seed has been deposited under Accession Number NCIMB 42445.

In another aspect the invention provides for a hybrid variety of *Allium ampeloprasum* var. *porrum* (L.) designated NUN 08412, plants produced from growing the seeds of the new variety NUN 08412 or plants produced from vegetative propagating a plant designated NUN 08412, and progeny of any of these. Especially, progeny retaining one or more (or all, or all except one, two or three) of the "distinguishing characteristics" or one or more (or all, or all except one, two or three) of the "essential morphological and physiological characteristics" or of (essentially) all physiological and morphological characteristics of NUN 08412 referred to herein, are encompassed herein as well as methods for producing these.

In one aspect, such progeny have (essentially) all the physiological and morphological characteristics of leek variety NUN 08412 when grown under the same environmental conditions.

Further, a leek leaf produced on a plant grown from a seed a representative sample of said seed has been deposited under Accession Number NCIMB 42455 is provided, as well as a leek leaf produced on a plant designated NUN 08412 or a progeny thereof.

In yet another embodiment of the invention, an Essentially Derived Variety of NUN 08412 having one, two or three physiological and/or morphological characteristics which are different from those of NUN 08412 and which otherwise has all the physiological and morphological characteristics of NUN 08412, wherein a representative sample of seed of variety NUN 08412 has been deposited under Accession Number NCIMB 42445, is provided.

Further, a vegetatively propagated plant of variety NUN 08412, or a part thereof, is provided having all the morphological and physiological characteristics of NUN 08412 when grown under the same environmental conditions.

Also a plant part derived from variety NUN 08412 is provided, wherein said plant part is selected from the group consisting of: (harvested) leaves or parts thereof, pollen, ovules, cells, leaves or parts thereof, petioles, shoots or parts thereof, stems or parts thereof, roots or parts thereof, cuttings, seeds, hypocotyl, cotyledon, flowers or parts thereof.

Definitions

"Leek" refers herein to plants of the species *Allium ampeloprasum* var. *porrum* (L.), also sometimes known as *Allium porrum*. Leek is a vegetable which belongs, along with the onion and garlic, to family Amaryffidaceae, subfamily Allioideae. Two related vegetables, the elephant garlic and kurrat, are also variant subspecies of *Allium ampeloprasum*, although different in their uses as food.

The edible part of the leek plant is a leaf or a bundle of leaf sheaths.

"Cultivated leek" refers to plants of *Allium ampeloprasum* var. *porrum* (L.), i.e. varieties, breeding lines or cultivars of the species *A. porrum*, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species.

"UPOV descriptors" are the plant variety descriptors described for leek in the "Guidelines for the Conduct of Tests for Distinctness, Uniformity and Stability, TG/85/7 (Geneva 2008), as published by UPOV (International Union for the Protection of New Varieties and Plants, available on the world wide web at upov.int) and which can be downloaded from the world wide web at upov.int/edocs/tgdocs/en/tg085.pdf and is herein incorporated by reference in its entirety.

"RHS" refers to the Royal Horticultural Society of England which publishes an official botanical color chart quantitatively identifying colors according to a defined numbering system, The chart may be purchased from Royal Horticulture Society Enterprise Ltd RHS Garden; Wisley, Woking; Surrey GU236QB, UK, e.g., the RHS colour chart: 2007 (The Royal Horticultural Society, charity No: 222879, PO Box 313 London SW1P2PE; sold by, e.g., TORSO-VERLAG, Obere Grüben 8•D-97877 Wertheim, Article-No.: Art62-00008 EAN-Nr.: 4250193402112).

As used herein, the term "plant" includes the whole plant or any parts or derivatives thereof, preferably having the same genetic makeup as the plant from which it is obtained, such as plant organs (e.g. harvested or non-harvested leaf or leaf sheath), plant cells, plant protoplasts, plant cell tissue cultures from which whole plants can be regenerated, plant calli, plant cell clumps, plant transplants, seedlings, hypocotyl, cotyledon, plant cells that are intact in plants, plant clones or micropropagations, or parts of plants (e.g. harvested tissues or organs), such as plant cuttings, vegetative propagations, embryos, pollen, ovules, fruits, flowers, leaves, seeds, clonally propagated plants, roots, stems, root tips, grafts, parts of any of these and the like. Also any developmental stage is included, such as seedlings, cuttings prior or after rooting, mature plants or leaves (e.g., at harvest).

"Harvested plant material" refers herein to plant parts (e.g. leaf or leaf sheath detached from the whole plant) which have been collected for further storage and/or further use.

"Harvested seeds" refers to seeds harvested from a line or variety, e.g. produced after self-fertilization or cross-fertilization and collected.

A plant having "(essentially) all the physiological and morphological characteristics" means a plant having essentially all or all the physiological and morphological characteristics when grown under the same environmental conditions of the plant of NUN 08412 from which it was derived, e.g. the progenitor plant, the parent, the recurrent parent, the plant used for tissue- or cell culture, etc. For example, the plant may have all characteristics mentioned in Table 1. In certain embodiments, the plant having "essentially all the physiological and morphological characteristics" are plants having all the physiological and morphological characteristics, except for certain characteristics, such as one, two or three, mentioned, e.g. the characteristic(s) derived from a converted or introduced gene or trait and/or except for the characteristics which differ in an EDV. So, the plant may have all characteristics mentioned in Table 1, except for one, two or three characteristics of Table 1, in which the plant may thus differ.

A plant having one or more or all "essential physiological and/or morphological characteristics" or one or more "distinguishing characteristics" (such as one, two, three, four or five) refers to a plant having (or retaining) one or more, or all, or retaining all except one, two or three of the distinguishing characteristics mentioned in Table 1 when grown under the same environmental conditions that distinguish NUN 08412 from the most similar varieties Pluston and Poulton such distinguishing characteristics being selected from (but not limited to): plant height (N 8412 is significantly taller than Pluston and Poulton); longer leaf blade length when using leaf blade length of the most similar varieties Pluston and Poulton as reference, more narrow leaf blade width when using leaf blade width of the most similar varieties Pluston and Poulton as reference; longer plant length (e.g., at harvest) compared to most similar varieties Pluston and Poulton; a different foliage attitude, i.e., leaves of NUN 08412 are erected while leaves of Pluston and Poulton are semi-erected when grown under the same environmental conditions; longer shaft length when using shaft length of the most similar varieties Pluston and Poulton as reference; a higher shaft length/diameter ratio compared to shaft length/diameter ratio of most similar varieties Pluston and Poulton. Especially leaf blade width, plant length and shaft length were considered by UPOV to be useful grouping characteristics for leek The physiological and/or morphological characteristics mentioned above are commonly evaluated at significance levels of 1%, 5%, 8% or 10% significance level, when measured under the same environmental conditions. For example, a progeny plant of NUN 08412 may have one or more (or all, or all except one, two or three) of the essential physiological and/or morphological characteristics of NUN 08412 listed in Table 1, or one or more or all (or all except one, two or three) of the distinguishing characteristics of NUN 08412 listed in Table 1 and above, as determined at the 1% or 5%, significance level when grown under the same environmental conditions.

As used herein, the term "variety" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

A variety is referred to as an "Essentially Derived Variety" (EDV) i.e., shall be deemed to be essentially derived from another variety, "the initial variety" when (i) it is predominantly derived from the initial variety, or from a variety that is itself predominantly derived from the initial variety, while retaining the expression of the essential characteristics that result from the genotype or combination of genotypes of the initial variety; (ii) it is clearly distinguishable from the initial variety; and (iii) except for the differences which result from the act of derivation, it conforms to the initial variety in the expression of the essential characteristics that result from the genotype or combination of genotypes of the initial variety. Thus, an EDV may be obtained for example by the selection of a natural or induced mutant, or of a somaclonal variant, the selection of a variant individual from plants of the initial variety, backcrossing, or transformation by genetic engineering.

"Plant line" is for example a breeding line which can be used to develop one or more varieties.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, protoplasts, meristematic cell, root, root tip, pistil, anther, flower, shoot tip, shoot, stem, petiole, etc. When a whole plant is regenerated by vegetative propagation, it is also referred to as a vegetative propagation.

"Selfing" refers to self-pollination of a plant, i.e., the transfer of pollen from the anther to the stigma of the same plant. "Crossing" refers to the mating of two parent plants.

"Average" refers herein to the arithmetic mean.

"Locus" (plural loci) refers to the specific location of a gene or DNA sequence on a chromosome. A locus may confer a specific trait.

"Allele" refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e. diploid, these chromosomes are referred to as homologous chromosomes. Diploid organisms have one copy of each gene (and therefore one allele) on each chromosome. If both alleles are the same, they are homozygotes. If the alleles are different, they are heterozygotes.

"Genotype" refers to the genetic composition of a cell or organism.

The term "traditional breeding techniques" encompasses herein crossing, selfing, selection, double haploid production, embryo rescue, protoplast fusion, marker assisted selection, mutation breeding etc. as known to the breeder (i.e. methods other than genetic modification/transformation/ transgenic methods), by which, for example, a genetically heritable trait can be transferred from one leek line or variety to another.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce progeny plants. Progeny plants which have the trait are then crossed to the recurrent parent. After several generations of backcrossing and/or selfing the recurrent parent comprises the trait of the donor. The plant generated in this way may be referred to as a "single trait converted plant".

"Progeny" as used herein refers to plants derived from a plant designated NUN 08412. Progeny may be derived by regeneration of cell culture or tissue culture or parts of a plant designated NUN 08412 or selfing of a plant designated NUN 08412 or by producing seeds of a plant designated NUN 08412 and growing plants thereof. In further embodiments, progeny may also encompass plants derived from crossing of at least one plant designated NUN 08412 with another leek plant of the same or another variety or (breeding) line, or with a wild leek plant, backcrossing, inserting of a locus into a plant or selecting a plant comprising a mutation or selecting a variant. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above. Especially progeny of NUN 08412 which are EDVs or which retain all (or all except 1, 2 or 3) physiological and/or morphological characteristics of NUN 08412 listed in Table 1, or which retain all (or all except 1, 2, or 3) of the distinguishing characteristics of NUN 08412 described elsewhere herein and in Table 1, are encompassed herein.

The terms "gene converted" or "conversion plant" in this context refer to leek plants which are developed by backcrossing wherein essentially all of the desired morphological and physiological characteristics of parent are recovered in addition to the one or more genes transferred into the parent via the backcrossing technique or via genetic engineering. Likewise a "Single Locus Converted (Conversion) Plant" refers to plants which are developed by plant breeding techniques comprising or consisting of backcrossing, wherein essentially all of the desired morphological and physiological characteristics of a leek variety are recovered in addition to the characteristics of the single locus having been transferred into the variety via the backcrossing technique and/or by genetic transformation.

"Transgene" or "chimeric gene" refers to a genetic locus comprising a DNA sequence which has been introduced into the genome of a leek plant by transformation. A plant comprising a transgene stably integrated into its genome is referred to as "transgenic plant".

The term "mean" refers to the arithmetic mean of several measurements. The skilled person understands that the appearance of a plant depends to some extent on the growing conditions of said plant. Thus, the skilled person will know typical growing conditions for Summer leeks described herein. The mean, if not indicated otherwise within this application, refers to the arithmetic mean of measurements on at least 10 different, randomly selected plants of a variety or line.

DRAWINGS

The drawings described herein are for illustration purposes only and are not intended to limit the scope of the present teachings in any way.

DETAILED DESCRIPTION

Figure 1:
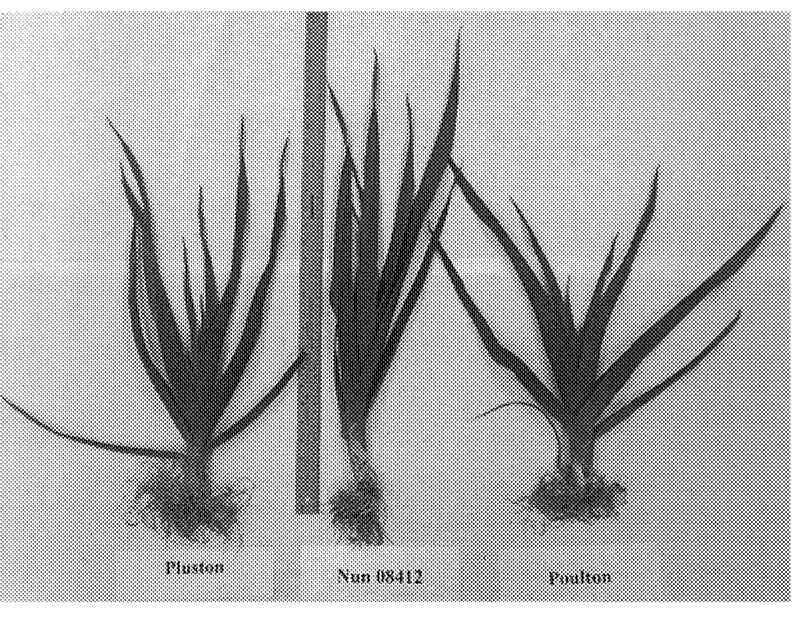
FIG. 1 shows a representative leek plant of NUN 08412, Pluston and Poulton shortly after harvest with different foliage attitude, plant height, plant length, shaft length and leaf blade length.

A number of characteristics are important to leek breeders including (but not limited to) (a) shaft length; (b) leaf blade length; (c) leaf blade width; (d) plant length; and (e) leaf blade color.

The present invention relates to an *Allium ampeloprasum* var. *porrum* (L.) leek type, referred to as NUN 08412, or progeny, or EDVs thereof, which has no bulb formation, a weak leaf blade bending, an erected foliage attitude and which is most similar to Pluston and Poulton which are both commercial varieties of Nunhems.

However, NUN 08412 can be easily distinguished from Pluston and Poulton. For example, the plant height in the field of NUN 08412 is higher than those of Pluston and Poulton (e.g., plant height NUN 08412: 62 cm, plant height of Pluston: 57.2 cm and plant height of Poulton: 51.8 cm when grown under the same environmental conditions), the foliage attitude of NUN 08412 is erected (see UPOV criteria) while the foliage attitude of Pluston and Poulton is semi-erected when grown under the same environmental conditions, the leaf blade width of NUN 08412 is more narrow than the leaf blade width in Pluston and Poulton when grown under the same environmental conditions, the shaft length of NUN 08412 is longer than the ones of Pluston or Poulon when grown under the same environmental conditions.

Furthermore, the new variety differs from variety Poulton, e.g., in that NUN 08412 has significantly longer leaves than Poulston (leaf blade length of NUN 08412: 50.3 cm, leaf blade length of Poulston: 41.2 cm when grown under the same environmental conditions).

Variety NUN 08412 provided herein differs from the most similar comparison varieties Pluston and Poulton, when grown under the same environmental conditions, in one or more characteristics (referred herein to as "distinguishing characteristics" or "distinguishing morphological and/or physiological characteristics" (or essential physiological and/or morphological characteristics) selected from:

the plant height in the field of NUN 08412 is higher than those of Pluston and Poulton (e.g., plant height NUN 08412: 62 cm, plant height of Pluston: 57.2 cm and plant height of Poulton: 51.8 cm when grown under the same environmental conditions), the foliage attitude of NUN 08412 is erected (see UPOV criteria) while the foliage attitude of Pluston and Poulton is semi-erected when grown under the same environmental conditions, the leaf blade length of NUN 08412 is longer than the leaf blade length of Pluston or Poulton (e.g., leaf blade length of NUN 08412: 50.3 cm, leaf blade length of Pluston: 47.8 cm, leaf blade length of Poulton: 41.2 cm when grown under the same environmental conditions), the leaf blade width of NUN 08412 is more narrow than the leaf blade width in Pluston and Poulton (e.g., leaf blade width of NUN 08412: 3.79 cm, leaf blade width of Pluston: 4.4 cm, leaf blade width of Poulton: 4.5 cm when grown under the same environmental conditions), the plant length of the harvested plant of NUN 08412 is taller than the plant length of the harvested plants of Pluston or Poulton (e.g., plant length of NUN 08412: 68 cm, plant length of Pluston: 63.7 cm, the plant length of Poulton: 55.5 cm when grown under the same environmental conditions), the shaft length of NUN 08412 is longer than the ones of Pluston or Poulton (e.g., shaft length of NUN 08412: 7.5 cm, shaft length of Pluston: 6.7 cm, shaft length of Poulton: 5.6 cm when grown under the same environmental conditions)

the shaft length/diameter ratio is higher in NUN 08412 than in Pluston or Poulton (e.g., length/diameter ratio of NUN 08412: 3,3; length/diameter ratio of Pluston: 2,7; length/diameter ratio of Poulton: 2.4 when grown under the same environmental conditions).

It is understood that "significant" differences refer to statistically significant differences, when comparing the characteristic between two plant lines or varieties when grown under the same conditions. Preferably at least about 10, 15, 20, 30, 40, 50 or more plants per line or variety are grown under the same conditions and characteristics are measured on at least about 10, 15, 20 or more randomly selected plant or plant parts to obtain averages. Thus, physiological and morphological characteristics or traits are commonly evaluated at a significance level of 1%, 5%, 8% or 10%, when measured in plants grown under the same environmental conditions. For example, two replications of 50 plants each, from which 20 plants or plant parts were randomly selected can be used to measure characteristics.

In one aspect, the invention provides seeds of the leek variety designated NUN 08412 wherein a representative sample of seeds of said variety was deposited under the Budapest Treaty, with Accession number NCIMB 42445.

Seeds of NUN 08412 are obtainable by crossing the male parent with the female parent and harvesting the seeds produced on the female parent. The resultant NUN 08412 seeds can be grown to produce NUN 08412 plants. In one embodiment a plurality of NUN 08412 seeds are packaged into small and/or large containers (e.g., bags, cartons, cans, etc.). The seeds may be primed and/or treated with various compounds, such as seed coatings and/or fungicides and/or insecticides.

Also provided are plants of leek variety NUN 08412, or a leaf, a bundle of leaf sheath or other plant part thereof, produced from seeds, wherein a representative sample of said seeds has been deposited under the Budapest Treaty, with Accession Number NCIMB 42445. Also included is a cell culture or tissue culture produced from such a plant or a plant regenerated from such a cell culture or tissue culture, said plant expressing all the morphological and physiological characteristics of NUN 08412, or all except one, two or three of the morphological and physiological characteristics of NUN 08412. In one embodiment said plant expressed all the distinguishing characteristics of NUN 08412, or all the distinguishing characteristics except one, two or three thereof. Plants of NUN 08412 can be produced by seeding directly in the ground (e.g., field) or by germinating the seeds in controlled environment conditions (e.g., greenhouses) and then transplanting the seedlings into the field.

In another aspect, the invention provides for a leek plant of leek variety NUN 08412, a representative sample of seed from said variety has been deposited under the Budapest Treaty, with Accession number NCIMB 42445.

In other aspects, the invention provides for a leaf or (a bundle of) leaf sheath(s) of leek variety NUN 08412, or a plant part, such as pollen, flowers, shoots or cuttings of variety NUN 08412 or parts thereof.

In still another aspect the invention provides a method of producing a leek plant, comprising crossing a plant of leek variety NUN 08412 with a second leek plant one or more times, and selecting progeny from said crossing.

In yet another aspect the invention provides a method of producing a leek plant, comprising selfing a plant of leek variety NUN 08412 one or more times, and selecting progeny from said selfing.

In other aspects, the invention provides for progeny of variety NUN 08412 such as progeny obtained by further breeding NUN 08412. Further breeding NUN 08412 includes selfing NUN 08412 one or more times and/or cross-pollinating NUN 08412 with another leek plant or variety one or more times. In particular, the invention provides for progeny that retain all (or all except one, two or three) of the essential morphological and physiological characteristics of NUN 08412 or that retain one or more or all (or all except one, two or three) of the distinguishing characteristics of the leek type described further above and when grown under the same environmental conditions. In another aspect, the invention provides for vegetative reproductions of the variety NUN 08412, or of progeny thereof, and the invention also provided for essentially derived varieties (EDVs) of NUN 08412, or of progeny thereof, and vegetative reproductions of such EDVs.

The morphological and/or physiological differences between plants according to the invention, i.e. NUN 08412 or progeny thereof, or an EDV thereof, and other known varieties can easily be established by growing NUN 08412 (or progeny or EDVs) next to the other varieties (in the same field, under the same environmental conditions), preferably in several locations which are suitable for said leek cultivation, and measuring morphological and/or physiological characteristics of a number of plants (e.g., to calculate an average value and to determine the variation range/uniformity within the variety). For example, trials can be carried out in Acampo, Calif., USA (N 38 degrees 07'261"/W 121 degrees 18'807", USA), whereby e.g., days from seeding to harvest, plant height, plant length, foliage attitude, shaft length, shaft diameter, shaft ratio length,/diameter, shaft bulb formation, leaf blade bending, leaf blade length, leaf blade width, leaf blade color, leaf blade intensity of color, leaf blade anthocyanin coloration, leaf blade waxiness, disease resistances and/or insect resistances can be measured and directly compared.

Morphological and/or physiological characteristics (and distinguishing characteristics which distinguish NUN 08412 from Pluston and/or Poulton) of NUN 08412, are provided in the Examples, in Table 1. Encompassed herein are also plants derivable from NUN 08412 (e.g. by selfings and/or crossing and/or backcrossing with NUN 08412 and/or mutant selection and/or natural variant selection and/or progeny thereof) comprising all (or all except one, two or three) of the physiological and/or morphological characteristics of NUN 01307 listed in Table 1 as determined at the 5% significance level when grown under the same environmental conditions and/or comprising one or more (or all; or all except one, two or three) of the distinguishing characteristics as determined at the 5% significance level when grown under the same environmental conditions.

Also at-harvest and/or post-harvest characteristics of leaves or bundles of leaf sheath can be compared. For example, cold storage holding quality (e.g., yellowing) can be measured using known methods.

The morphological and/or physiological characteristics may vary somewhat with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart on the world wide web at rhs.org.uk/Plants/RHS-Publications/RHS-colour-charts).

In a preferred embodiment, the invention provides for leek leaves of variety NUN 08412, or a part of the leaves. In another embodiment, the invention provides for a container comprising or consisting of a plurality of harvested leek leaves or bundle of leaf sheaths of NUN 08412, or progeny thereof, or a derived variety, such as an EDV.

In yet a further embodiment, the invention provides for a method of producing a new leek plant. The method comprises crossing a plant of the invention NUN 08412 or an EDV thereof or a progeny plant thereof, either as male or as female parent, with a second leek plant (or a wild relative of leek) one or more times, and/or selfing a leek plant according to the invention i.e. NUN 08412 or an EDV thereof or a progeny plant thereof, one or more times, and selecting progeny from said crossing and/or selfing. In one embodiment, the second leek plant is an *A. porrum* plant.

In one embodiment, progeny are either the generation (seeds) produced from the first cross (F1) or selfing (S1), or any further generation produced by crossing and/or selfing (F2, F3, etc.) and/or backcrossing (BC1, BC2, etc.) one or more selected plants of the F1 and/or S1 and/or BC1 generation (or plants of any further generation, e.g. the F2) with another leek plant (and/or with a wild relative of leek). Progeny may have all (or all except one, two or three) of the physiological and/or morphological characteristics of leek variety NUN 08412 when grown under the same environmental conditions and/or progeny may have (be selected for having) one or more, or all (or all except one, two or three) of the distinguishing characteristics of leeks of the invention. Using common breeding methods such as backcrossing or recurrent selection, one or more specific characteristics may be introduced into NUN 08412, to provide an EDV of NUN 08412.

The invention provides for methods of producing varieties which retain all (or all except one, two or three) of the morphological and/or physiological characteristics of NUN 08412 or that retain all (or all except one, two or three) of the distinguishing characteristics of NUN 08412. The invention provides also for methods of producing EDVs (Essentially Derived Varieties) of NUN 08412 which differ from NUN 08412 in one, two, three or more morphological and/or physiological characteristics, but which are still genetically closely related to NUN 08412. The relatedness can, for example be determined by fingerprinting techniques (e.g., making use of isozyme markers and/or molecular markers such as SNP markers, AFLP markers, microsatellites, SSR markers, minisatellites, RAPD markers, RFLP markers and others). A plant is "closely related" to NUN 08412 if its DNA fingerprint is at least 80%, 90%, 95% or 98% identical to the fingerprint of NUN 08412. In one embodiment AFLP markers are used for DNA fingerprinting (Vos et al. 1995, Nucleic Acid Research 23: 4407-4414) or other markers, such as microsatellite markers. A closely related plant may have a Jaccard's Similarity index of at least about 0.8, preferably at least about 0.9, 0.95, 0.95, 0.96, 0.97, 0.98 or more (Staub et al 2000, Euphytica 115: 225-241). The invention also provides plants and varieties obtained by these methods. In one embodiment, relatedness and whether a variety is an EDV of NUN 08412, may be determined according to the Variety Tracer method of the Nak Tuinbouw (on the world wide web at naktuinbouw.nil/en/topic/identification-using-dna).

By crossing and/or selfing also (one or more) single traits may be introduced into the variety of the invention i.e. NUN 08412 (e.g., using backcrossing breeding schemes), while retaining the remaining morphological and/or physiological characteristics of NUN 08412 and/or while retaining one or more (or all except one, two or three) of the distinguishing characteristics. A single trait converted plant may thereby be produced. For example, disease resistance genes may be introduced, genes responsible for one or more quality traits, yield, etc. Both single genes (dominant or recessive) and one or more QTLs (quantitative trait loci) may be transferred into NUN 08412 by breeding with NUN 08412.

Any pest or disease resistance genes may be introduced into a plant according to the invention, i.e. NUN 08412, progeny thereof or into an EDV of NUN 08412. Resistance to one or more of the following diseases is preferably introduced into plants of the invention: Bacterial Wilt, Root Rot, Crown Blight, Leek Rust, Powdery Mildew, *Verticillum* Wilt, Sulphur Burn, Scab, Waterleek Mosaic, Downy Mildew, *Fusarium oxysporum* f.sp. leekis (Fom) race 0, *Fusarium oxysporum* f.sp. leekis (Fom) race 1, *Fusarium oxysporum* f.sp. leekis (Fom) race 2, *Fusarium oxysporum* f.sp. leekis (Fom) race 1-2, *Fusarium* Wilt R2, Root Knot (Nematode), Anthracnose, Cucumber Mosiac, and Squash Mosaic, *Alternaria porri, Phytophthora porri* and Leek Yellow Stripe Virus.

Resistance to one or more of the following pests is preferably present or introduced into plants of the invention: Aphid resistance, Pickle Worm, Darkling Ground Beetle, Banded Cucumber Beetle, Mite, Western Spotted Cucumber Beetle, Leek Leafhopper, Leek Worm, Western Striped Cucumber Beetle or Leek Leafminer, *Thrips tabaci*, Leek moth and Onion fly.

Other resistance genes, against pathogenic viruses, fungi, bacteria or pests may also be introduced.

Thus, invention also provides a method for developing a leek plant in a leek breeding program, using a leek plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 08412 or progeny thereof, or an EDV thereof, with a different leek plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Martin et al. 2008, Australian Journal of Crop Science 1(2): 43-46). For breeding methods in general see Principles of Plant Genetics and Breeding, 2007, George Acquaah, Blackwell Publishing, ISBN-13: 978-1-4051-3646-4.

The invention thus also provides a method of introducing a single locus conversion, or single trait conversion, into a leek plant according to the invention and/or into NUN 08412 comprising:
(a) crossing a leek plant of variety NUN 08412, a representative sample of seed of said variety having been deposited under Accession Number NCIMB 42445, with a second leek plant comprising a desired single locus to produce F1 progeny plants;
(b) selecting F1 progeny plants that have the single locus to produce selected F1 progeny plants;
(c) crossing the selected progeny plants with a plant of NUN 08412, to produce backcross progeny plants;
(d) selecting backcross progeny plants that have the single locus and one or more or all (or all except one, two or three) of the distinguishing characteristics of leeks according to the invention and/or all (or all except one, two or three) of the physiological and/or morphological characteristics of NUN 08412 to produce selected backcross progeny plants; and
(e) repeating steps (c) and (d) one or more times in succession to produce selected second, third, fourth or higher backcross progeny plants that comprise the single locus and otherwise one or more or all distinguishing characteristics of the leeks according to the invention and/or comprise all of the physiological and morphological characteristics of NUN 08412, when grown in the same environmental conditions.

The above method is provided, wherein the single locus confers a trait, wherein the trait is pest resistance or disease resistance.

In one embodiment the trait is disease resistance and the resistance is conferred to Bacterial Wilt, Root Rot, Crown Blight, Leek Rust, Powdery Mildew, *Verticillum* Wilt, Sulphur Burn, Scab, Waterleek Mosaic, Downy Mildew, *Fusarium oxysporum* f.sp. leekis (Fom) race 0, *Fusarium oxysporum* f.sp. leekis (Fom) race 1, *Fusarium oxysporum* f.sp. leekis (Fom) race 2, *Fusarium oxysporum* f.sp. leekis (Fom) race 1-2 *Fusarium* Wilt R2, Root Knot (Nematode), Anthracnose, Cucumber Mosiac, and Squash Mosaic, *Alternaria porri, Phytophthora porri* and Leek Yellow Stripe Virus.

In one embodiment the trait is pest resistance and the resistance is conferred to Aphid resistance, Pickle Worm, Darkling Ground Beetle, Banded Cucumber Beetle, Mite, Western Spotted Cucumber Beetle, Leek Leafhopper, Leek Worm, Western Striped Cucumber Beetle or Leek Leafminer, *Thrips tabaci*, Leek moth and Onion fly.

The invention also provides a leek plant comprising at least a first set of the chromosomes of leek line NUN 08412, a sample of seed of said line having been deposited under Accession Number NCIMB 42445; further provided is a leek plant comprising a single locus conversion, wherein said leek plant has essentially all of the morphological and/or physiological characteristics of the leek plant comprising at least a first set of the chromosomes of leek variety NUN 08412. In another embodiment, this single locus conversion confers a trait selected from the group consisting of male sterility, herbicide tolerance, insect resistance, pest resistance, disease resistance, environmental stress tolerance, modified carbohydrate metabolism and modified protein metabolism.

In one embodiment, NUN 08412 may also be mutated (by e.g. irradiation, chemical mutagenesis, heat treatment, etc.) and mutated seeds or plants may be selected in order to change one or more characteristics of NUN 08412, e.g. one, two, three or more of the essential physiological and/or morphological characteristics of NUN 08412 may be changed. The one, two, three or more changed characteristics may be one, two or three of the distinguishing characteristics of NUN 08412. Also natural mutants or natural variants of NUN 08412 may be identified and used in breeding. Methods such as TILLING and/or EcoTILLING may be applied to leek populations in order to identify mutants. Similarly, NUN 08412 may be transformed and regenerated, whereby one or more chimeric genes are introduced into the variety or progeny thereof or into an EDV thereof. Transformation can be carried out using standard methods, such as Agrobacterium tumefaciens mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 08412, or progeny thereof, by transforming NUN 08412 or progeny thereof with a transgene that confers the desired trait, wherein the transformed plant retains all the phenotypic and/or morphological and/or physiological characteristics of NUN 08412 or the progeny thereof and contains the desired trait. Thus, also a transgenic leek plant comprising a transgene conferring a desired trait and further comprising all (or all except one two or three) of the morphological and/or physiological characteristics of NUN 08412, or further comprising all (or all except one, two or three) of the distinguishing characteristics of NUN 08412, is provided herein.

The invention also provides for progeny of leek variety NUN 08412 obtained by further breeding with NUN 08412. In one aspect progeny are F1 progeny obtained by crossing NUN 08412 with another plant; or S1 progeny obtained by selfing NUN 08412. Also encompassed are F2 progeny obtained by selfing the F1 plants or by back-crossing F1 plants with NUN 08412. "Further breeding" encompasses traditional breeding (e.g., selfing, crossing, backcrossing), marker assisted breeding, and/or mutation breeding. In one embodiment, the progeny have one or more or all of the distinguishing characteristics mentioned further above when grown under the same environmental conditions. In a further embodiment the progeny have all the physiological and/or morphological characteristics of variety NUN 08412 when grown under the same environmental conditions. In another embodiment the progeny are EDVs and/or have one, two, or three distinct traits (qualitative or quantitative) introduced into NUN 08412, while retaining all the other physiological and morphological characteristics of variety NUN 08412 when grown under the same environmental conditions.

An EDV is an Essentially Derived Variety of NUN 08412 having one, two or three physiological and/or morphological characteristics which are different from those of NUN 08412 and which otherwise has all the physiological and morphological characteristics of NUN 08412, wherein a representative sample of seed of variety NUN 08412, has been deposited under Accession Number NCIMB 42445. In particular variants which differ from NUN 08412 in one, two or three of the characteristics mentioned in Table 1 are encompassed.

In one aspect, the EDV differs from NUN 08412 in one, two or three of the distinguishing morphological and/or physiological characteristics selected from: i) plant height, ii) plant length, iii) foliage attitude, iv) shaft length, v) shaft ratio length/diameter, vi) leaf blade length, vii) leaf blade width.

In another embodiment the EDV may differ from NUN 08412 in one, two or three morphological and/or physiological characteristic other than the "distinguishing morphological and/or physiological characteristics" (or essential physiological and/or morphological characteristics) of NUN 08412 for example selected from (but not limited to): i) days from seeding to harvest, ii) shaft diameter, iii) shaft bulb formation, iv) leaf blade bending, v) leaf blade color, vi) leaf blade intensity of coloration, vii) leaf blade anthocyanin coloration, viii) leaf blade waxiness or other characteristics.

Leeks according to the invention, such as the variety NUN 08412, or its progeny or an EDV of NUN 08412, can also be reproduced using vegetative reproduction methods. Therefore, the invention provides for a method of producing plants, or a part thereof, of variety NUN 08412, or of progeny thereof, or of an EDV of NUN 08412, comprising vegetative propagation of variety NUN 08412 or of progeny thereof, or of an EDV of NUN 08412. Vegetative propagation comprises regenerating a whole plant from a part of variety NUN 08412 (or from its progeny or from an EDV of NUN 08412), such as a cutting, a cell culture or a tissue culture.

The invention also provides for a vegetatively propagated plant of variety NUN 08412 (or from its progeny or from an EDV of NUN 08412), or a part thereof, having one or more distinguishing characteristics or all the morphological and physiological characteristics of NUN 08412 (except for the characteristics differing in the EDV), when grown under the same environmental conditions.

Parts of NUN 08412 (or from its progeny or from an EDV of NUN 08412) encompass any cells, tissues, organs obtainable from the seedlings or plants, such as but not limited to: leek leaves or parts thereof, cuttings, hypocotyl, cotyledon, pollen, flowers, anthers, embryos, ovaries, and the like. Such parts can be stored and/or processed further. Encompassed are therefore also food or feed products comprising one or more of such parts, such as fresh, dried, frozen leek leaves or parts thereof, etc. from NUN 08412 or from progeny thereof, or from a derived variety, such as an EDV.

In one aspect, haploid plants and/or double haploid plants of NUN 08412, or an EDV of NUN 08412, or progeny of any of these, are encompassed herein. Haploid and double haploid (DH) plants can, for example, be produced by cell or tissue culture and chromosome doubling agents and regeneration into a whole plant. For DH production chromosome doubling may be induced using known methods, such as colchicine treatment or the like.

In one embodiment, the invention provides for extracts of a plant described herein and compositions comprising or consisting of such extracts. In a preferred embodiment, the extract consists of or comprises tissue of a plant described herein or is obtained from such tissue.

The invention also provides for a food or feed product comprising or consisting of a plant part described herein preferably a leek leaf or part thereof and/or an extract from a plant part described herein. The food or feed product may be fresh or processed, e.g., canned, steamed, boiled, fried, blanched and/or frozen, etc.

For example, containers such as cans, boxes, crates, bags, cartons, Modified Atmosphere Packagings, films (e.g. biodegradable films), etc. comprising plant parts of plants (fresh and/or processed) described herein are also provided herein.

Marketable leek bundles of leaf sheaths are generally sorted by size and quality after harvest.

All documents (e.g., patent publications) are herein incorporated by reference in their entirety.

EXAMPLES

Development of NUN 08412

The hybrid NUN 08412 was developed from a male and female proprietary inbred line of Nunhems. The female and male parents were crossed to produce hybrid (F1) seeds of NUN 08412. The seeds of NUN 08412 can be grown to produce hybrid plants and parts thereof (e.g. leek leaves). The hybrid NUN 08412 can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant concluded that NUN 08412 is uniform and stable.

Deposit Information

A total of 2500 seeds of the hybrid variety NUN 08412 were deposited according to the Budapest Treaty by Nunhems B.V. on Jul. 29, 2015, at the NCIMB Ltd., Ferguson Building, Craibstone Estate, Bucksburn, Aberdeen AB21 9YA, United Kingdom (NCIMB). The deposit has been assigned Accession Number NCIMB 42445.

A deposit of NUN 08412 and of the male and female parent line is also maintained at Nunhems B.V. Access to the deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

Most similar varieties to NUN 08412 are Pluston and Poulston, commercial varieties from Nunhems B.V. In Table 1 a comparison between NUN 08412 and most similar varieties Pluston and Poulton is shown based on a trial in the USA. Trial location: Acampo, Calif. USA, (coordinates: 38° 07'261"N, −121° 18'80547"W), USA 2011/2012. Planting date: seeding date Nov. 6, 2011, transplanting date Nov. 4, 2011 and harvested Mar. 13, 2012.

Two replications of 50 plants each, from which 20 plants or plant parts were randomly selected to measure characteristics. In Table 1 the USDA descriptors of NUN 08412 (this application) and reference Pluston (commercial variety) and Poulton (commercial variety) are summarized.

TABLE 1 morphological and/or physiological characteristics of NUN 08412 and
comparative varieties, including distinguishing characteristics of NUN 08412 (in bold)

| Descriptor | Application Variety NUN 08412 | Comparison Variety Pluston | Comparison Variety Poulton |
|---|---|---|---|
| 1. Days From Seeding to Harvest | 128 | 128 | 128 |
| 2. PLANT | | | |
| Plant Height | 62 cm | 57.2 cm | 51.8 cm |
| Plant length (at harvest) | 68 cm | 63.7 cm | 55.5 cm |
| Foliage attitude | 1 | 2 | 2 |
| 1 = erect (Rese); | | | |
| 2 = semi-erect (Linx); | | | |
| 3 = horizontal (De Carentan 2) | | | |
| 3. SHAFT | | | |
| Shaft length (base of the plant above roots to divergence of the first non-senescing leaf) | 7.5 cm | 6.7 cm | 5.6 cm |
| Shaft diameter | 2.3 cm | 2.5 cm | 2.3 cm |
| Shaft ratio length/diameter | 3.3 | 2.7 | 2.4 |
| Shaft bulb formation | 1 | 1 | 1 |
| 1 = absent or very weak; | | | |
| 2 = weak; | | | |
| 3 = medium; | | | |
| 4 = strong; | | | |
| 5 = very strong | | | |
| 5. LEAF BLADE | | | |
| Leaf blade bending | 3 | 3 | 3 |
| 1 = strong (Blauwgroene Winter); | | | |
| 2 = medium; (Flextan) | | | |
| 3 = weak (Bell) | | | |
| Leaf blade length: | 50.3 cm | 47.8 cm | 41.2 cm |
| Leaf blade width: | 3.8 cm | 4.4 cm | 4.5 cm |
| Leaf blade color: | 3 | 3 | 3 |
| 1 = yellow green (Jaune gros du Poitou); | | | |
| 2 = green (Premier); | | | |
| 3 = grey green (Zwitserse Reuzen); | | | |
| 4 = blue green (Blauwgroene Winter) | | | |
| Color Chart Name | RHS | RHS | RHS |
| Color Chart Code (GG = Green Group; YGG = Yellow Green Group) | 122A | 122A | 122A |
| Leaf blade intensity of color | 3 | 3 | 3 |
| 1 = light; | | | |
| 2 = medium | | | |
| 3 = dark | | | |
| Leaf blade anthocyanin coloration | 1 | 1 | 1 |
| 1 = absent or very weak; | | | |
| 2 = weak; | | | |
| 3 = medium; | | | |
| 4 = strong; | | | |
| 5 = very strong | | | |
| Leaf blade waxiness | 3 | 3 | 3 |
| 1 = absent or very weak (Kingston); | | | |
| 2 = weak (Carlton); | | | |
| 3 = medium (Linx); | | | |
| 4 = strong (Flextan); | | | |
| 5 = very strong | | | |

These are typical values. Values may vary due to environment.

References on the world wide web at upov.int/edocs/tgdocs/en/tg085.pdf.

on the world wide web at rhs.org.uk/Plants/RHS-Publications/RHS-colour-charts.

Vos et al. 1995, Nucleic Acid Research 23: 4407-4414).

Staub et al 2000, Euphytica 115: 225-241.

on the world wide web at naktuinbouw.nl/en/topic/identification-using-dna.

The invention claimed is:

1. A seed of leek variety NUN 08412, wherein a representative sample of said seed has been deposited under Accession Number NCIMB 42445.

2. A plant of leek variety NUN 08412, or a part thereof, wherein a representative sample of seed of said variety has been deposited under Accession Number NCIMB 42445.

3. A leaf of leek variety NUN 08412, or a plant part produced from the plant of claim 2, wherein said plant part is selected from the group consisting of: parts of a leaf of leek variety NUN 08412, cells, petioles, shoots or parts thereof, stems, or parts thereof, roots or parts thereof, cuttings, hypocotyl and cotyledon.

4. A method of producing a leek plant, said method comprising crossing the plant of claim 2 with a second leek plant one or more times, and selecting progeny from said crossing.

5. A method of producing a leek plant comprising selfing the plant of claim 2 one or more times, and selecting progeny from said selfing.

6. A method of producing plants, or a part thereof, of variety NUN 08412 comprising vegetative propagation of variety NUN 08412.

7. The method of claim 6, wherein said vegetative propagation comprises regenerating a whole plant from a part of variety NUN 08412.

8. The method of claim 7, wherein said part is a cutting, a cell culture or a tissue culture.

9. A vegetative propagated plant of variety NUN 08412, or a part thereof, having all the morphological and physiological characteristics of NUN 08412 when grown under the same environmental conditions.

10. A plant part of the plant of claim 9, wherein said plant part is selected from the group consisting of leaves or parts thereof, cells, petioles, shoots or parts thereof, stems or parts thereof, roots or parts thereof and cuttings or parts thereof.

11. A food or feed product comprising a plant part of claim 10.

12. The food or feed product of claim 11, wherein said plant part is fresh or processed.

13. A leek plant produced by growing the seed of claim 1.

14. A method of producing a leek plant having a desired trait, wherein the method comprises transforming the leek plant of claim 2 with a transgene that confers the desired trait, wherein the transformed plant retains all the phenotypic and morphological characteristics of variety NUN 08412, a representative sample of seed of said variety NUN 08412 having been deposited under Accession Number NCIMB 42445, and contains the desired trait.

15. A leek plant produced by the method of claim 14, wherein the plant comprises the desired trait and all of the physiological and morphological characteristics of NUN 08412.

16. A cell or tissue culture produced from a plant of claim 2.

17. A leek plant regenerated from a cell or tissue culture of claim 16, said plant expressing all the morphological and physiological characteristics of NUN 08412, wherein a representative sample having been deposited under Accession Number NCIMB 42445.

18. A plant part of the plant of claim 2, wherein said plant part is a harvested leaf or a part thereof, a cell, a petiole, a shoot or a part thereof, a stem or a part thereof, a root or a part thereof, or a cutting.

19. A food or feed product comprising the plant part of claim 18.

* * * * *